Figure 1:
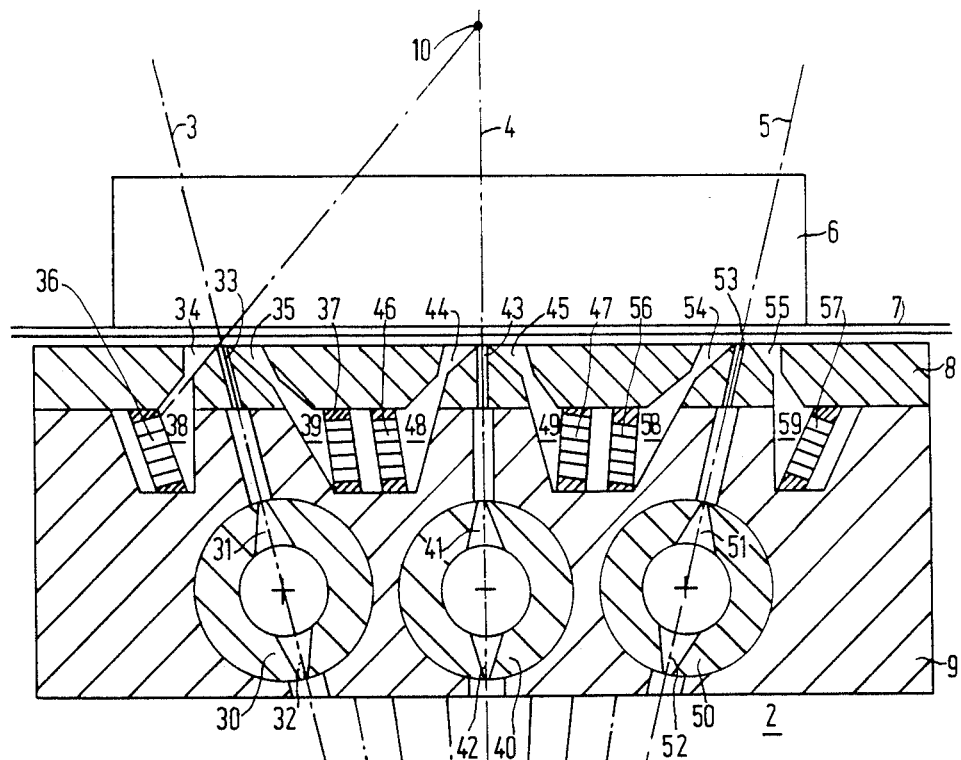

United States Patent [19]
Harding

[11] Patent Number: 4,750,196
[45] Date of Patent: Jun. 7, 1988

[54] DEVICE FOR EXAMINING A BODY BY MEANS OF GAMMA RAYS OR X-RAYS

[75] Inventor: Geoffrey Harding, Hamburg, Fed. Rep. of Germany

[73] Assignee: U.S. Philips Corp., New York, N.Y.

[21] Appl. No.: 798,096

[22] Filed: Nov. 14, 1985

[30] Foreign Application Priority Data

Nov. 27, 1984 [DE] Fed. Rep. of Germany ....... 3443095

[51] Int. Cl.$^4$ ..................... G21K 1/02; G01N 23/201; G01N 23/203
[52] U.S. Cl. ..................................... 378/87; 378/147; 378/149; 378/86
[58] Field of Search ....................... 378/86, 87, 88, 89, 378/3, 6, 146, 149, 150

[56] References Cited

U.S. PATENT DOCUMENTS 3,505,520 10/1967 Stewart et al. ..................... 378/88
4,423,522 12/1983 Harding .............................. 378/6
4,480,332 10/1984 Strecker ............................. 378/87

Primary Examiner—Carolyn E. Fields
Assistant Examiner—Joseph A. Hynds
Attorney, Agent, or Firm—Paul R. Miller

[57] ABSTRACT

The invention relates to a device for examining a body by means of gamma rays or X-rays, in which a body to be examined is irradiated by a plurality of primary beams having a comparatively small cross-section. The scattered radiation produced is intercepted by detector devices, at least one of which is associated each time with a respective primary beam, and the detector device and an associated slit which images the primary beam on the detector device is arranged so that the detector device is struck essentially only by scattered radiation from this one primary beam. Preferably, the detectors are arranged between the body to be examined and the radiation source, so that they can intercept only the back-scattered radiation.

7 Claims, 1 Drawing Sheet

DEVICE FOR EXAMINING A BODY BY MEANS OF GAMMA RAYS OR X-RAYS

The invention relats to a device for examining a body by means of gamma rays or X-rays which includes a radiation source, a diaphragm device which is disposed between the radiation source and the body and which comprises an aperture for forming a primary beam having a small cross-section, and a detector device on which the scattered radiation produced in the body by the primary beam is incident through a slit. A device of this kind is known from DE-PS No. 27 13 581.

The slit maps the region irradiated by the primary beam on the (spatial resolution) detector device so that each part of the primary beam is associated with a given spatial region of the detector device. The scatter densitity distribution along the primary beam can thus be determined by means of a single measurement. In order to determine the scatter density distribution in a two-dimensional or three-dimensional region, a relative displacement is required between the radiation source, the diaphragm device and the detector device on the one side and the body to be examined on the other side with the displacement being required in one or two directions perpendicular to the direction of theprimary beam. Determination of the scatter density in a multi-dimensional region is, therefore, comparatively time-consuming. The required period of time could be reduced by reducing the individual measurement periods for determining the scatter density along a primary beam, but in that case the signal-to-noise ratio would suffer.

It is the object of the invention to construct a device of the kind set forth in such a manner that the examination times can be reduced during the examination of a multi-dimensional region, without affecting the signal-to-noise ratio.

Using a device of the kind set forth, this object is achieved in that the diaphragm device includes a plurality of apertures for a plurality of primary beams, with each primary beam there being associated at least one slit and one detector device for intercepting the scattered radiation produced by the primary beam passing through the aperture and with the detector devices being shielded against radiation in such a manner that they cannot be struck by the scattered radiation of the respective other primary beams other than through the associated slit. The examination times can thus be reduced by a factor which corresponds to the number of apertures or primary beams.

In a device of this kind it is unavoidable that a detector device detects, through the associated slit, the scattered radiation of a primary beam which passes through an aperture which is not associated with the relevant detector device. Disturbing superpositions can thus occur.

In a further embodiment of the invention these superposition effects can be reduced in that the detector device is arranged between the body to be examined and the radiation source.

The detector devices can now intercept only the radiation which is scattered backwards. Because the primary beams emitted by the radiation source diverge, the distance between two points in different primary beams whose scattered radiation is intercepted by the same part of a detector device is very large, so that the scattered radiation produced in one of the two points is attenuated by the body to such an extent that disturbing superpositions are substantially precluded.

In a further embodiment of the invention the diaphragm device includes a movable, preferably rotatable member which is constructed so that the primary beams are shifted in parallel directions in reaction to a motion or rotation. The primary beams can thus be shifted merely by movement or rotation of the diaphragm member, so that a plurality of two-dimensional regions of the body can be scanned.

Figure 2:
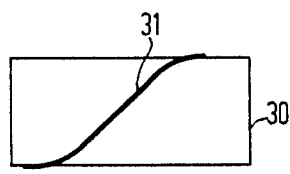

The invention will be described in detail hereinafter with reference to the drawing. Therein:

FIG. 1 is a cross-sectional view of a device in accordance with the invention, and FIG. 2 is a side elevation of a part of this device.

A substantially point-shaped radiation source 1, for examaple an X-ray source (not shown), emits a radiation beam which diverges in the plane of drawing as well as in the direction perpendicular thereto and which is incident on a diaphragm and measurement device 2 which forms three primary beams 3, 4, 5 having a small cross-section from the radiation beam. The three diverging primary beams pass through the object 6 to be examined, for example a workpiece which is arranged on a plate 7 which hardly absorbs the radiation.

The diaphragm and measurement device includes a plate-shaped upper section 8 and a parallelepiped lower section 9 in which three hollow rollers 30, 40 and 50 are arranged so as to be rotatable about their longitudinal axes. These longitudinal axes extend parallel to one another in a horizontal plane which is perpendicular to the plane of drawing. The longitudinal axes do not extend exactly perpendicularly to the plane of drawing; these deviations from the perpendicular direction are determined by the divergence of the radiation. Each of the three hollow rollers includes two narrow apertures 31 and 32, 41 and 42, and 51 and 52, respectively, which are distributed over their circumference at an angle of 180° and which widen conically in the direction of the center of the rollers in order to avoid shielding of the radiation at the edges due to the divergence of the radiation.

As appears from FIG. 2 which shows the roller 30 in a side elevation, the aperture 31 forms part of a slit which extends through the wall of the roller in the form of a spiral. The same is applicable to all other apertures with the two spiral slits in each roller being staggered exactly 180° with respect to each other. In each angular position of the roller (with respect to its axis of rotation), therefore, a location is formed on the longitudinal axis where the radiation emitted by the radiation source can pass through the upper and the lower spiral-shaped slit, so that behind the roller (viewed from the radiation source) there is formed a (primary) beam having a small cross-section which can also pass the lower section because the latter is provided with a slit-shaped aperture in a comparatively large region on both sides of a plane containing the point-shaped radiation source 1 and the axis of the roller. The primary beams 3, 4 and 5 thus formed pass through the upper section 8 via narrow slit-shaped apertures 33, 43 and 53 which extend perpendicularly to the plane of drawing. In the body 6 to be examined the primary beams produce scattered radiation which propagates, around the primary beam, to the front, the side and the rear. The scattered back radiation reaches, by slits 34, 35; 44, 45; 54, 55 a respective spatial resolution detector device 36, 37; 46, 47; 56, 57 which is situated in a respective chamber 38, 39; 48, 49; 58, 59. Every two chambers and the detectors accommodated therein are situated one on each side of a plane which contains the primary beam and which extends perpendicularly to the plane of drawing, so that the detector devices accommodated therein essentially intercept only the scattered radiation of the primary beam determining the relevant plane. For example, the detector devices 36 and 37 intercept the scattered radiation in the primary beam 3, the detector devices 46 and 47 intercept the scattered radiation in the primary beam 4, etc.

Cross-sections of the device 8, 9 and the parts contained therein in planes parallel to the plane of drawing are identical, except for the deflection device with the rollers which do not extend exactly perpendicularly to the plane of drawing.

Each detector device may consist of several detectors, for example crystal detectors, and is arranged, together with the associated slit, so that a part of the primary beam is imaged on the detector device through the slit as described in DE-PS No. 27 13 581. The present device is constructed so that it can intercept the scattered radiation only in a lower section which starts approximately at the plate 7 and which ends at some distance therefrom. Consequently, in a thick body the scattered radiation in an upper section cannot be intercepted; however, this is not a drawback when the aim is to determine inhomogeneities in the lower section.

This arrangement of the slits (for example, 34) and the associated detector device (for example, 36), however, implies that the detector device can also "see" a neightboring primary beam (for example, 4) through the slit. Scattered radiation produced in the point 10 by the primary beam 4 could thus reach, through the slit 34, the upper detector or the upper detector section of the detector device 36, thus falsifying the measurement when upon reconstruction it is assumed that the scattered radiation intercepted by the detector device 36 is produced exclusively at the area of the primary beam 3.

However, this falsification is only slight, because (assuming that the body is indeed so thick that a scatter center is situated in the point 10) the scattered radiation emerging from this point is absorbed to a great extent by the body 6. Morover, the primary beam 4 has already been attenuated before it reaches the point 10. The scatter intensity emerging from the point 10 and reaching the detector device 36, therefore, will be negligibly small. This is achieved on the one hand in that the back-scattered radiation is intercepted, and on the other hand in that the angle between neighboring primary beams 3 and 4 or 4 and 5 is comparatively large (approximately 15°) and in that invarably only in the lower section the scattered radiation is intercepted which is only comparatively slightly attenuated by the body 6. The fact that only the back-scattered radiation is intercepted, moreover, results in a compact construction because, as appears from the drawing, the diaphragm devices 30, 33 . . . 50, 53 and the detector devices 36, 37 . . . 56, 57 can be structurally combined.

In order to enable a two-dimensional region to be scanned by means of each primary beam 3, 4, 5, a relative displacement between the object 6 and the primary beam is required. This can be realized most simply by rotation of the rollers 30, 40 and 50 about their axes each time by the same amount. The location in which the radiation can pass through both slit-shaped apertures of a roller is then shifted perpendicularly to the plane of drawing, so that the plane defined by the primary beams 3, 4 and 5 is rotated about the point defined by the radiation source 1. A three-dimensional region is covered when the object 6 on the one side and the diaphragm and detector device, together with the radiation source, on the other side are displaced with respect to each other in the horizontal direction.

In the embodiment shown in the drawing, the displacement of the primary beams 3, 4 and 5 in the direction perpendicular to the plane of drawing is achieved in that each of the three rollers is rotated by a given angular amount. Instead of the rollers, use could alternatively be made of a diaphragm plate which is rotatable about a vertical axis and which is provided with a slit-shaped apertureextending approximately perpendicularly to the slit-shaped apertures 33, 43 and 53, for example as known from DE OS No. 30 32 801 corresponding to U.S. Pat. No. 4,423,522. In that case a primary beam is formed on the one hand by the slit-shaped aperture in the rotatable diaphragm plate and on the other hand by each time by one of the apertures 33, 43 or 53. In the embodiment shown in the drawing, the rollers 30, 40 or 50 would already suffice for this purpose, but it would be useful to restrict the lateral expansion of the primary beam 3, 4 or 5 by the slit-shaped apertures 33, 43 or 53.

What is claimed is:

1. A device for examining a body by gamma rays or X-rays comprising a radiation source, a diaphragm device arranged between said radiation source and said body, wherein said diaphragm device comprises a plurality of apertures for forming a plurality of primary beams, each of said primary beams having associated at least one slit and at least one detector device in said diaphragm device for intercepting scattered radiation from said primary beam passing through said diaphragm device, said at least one detector device being shielded to prevent striking of said at least one slit and at least one detector device by scattered radiation from other primary beams, wherein said at least one detector device is disposed between said radiation source and said body to be examined.

2. A device according to claim 1, wherein a common housing encloses said diaphragm device and said at least one detector device, said common housing including said plurality of apertures for said primary beams, and a plurality of chambers provided with slits at a side of said common housing remote from said radiation source, said scattered radiation reaching said at least one detector device by said slits.

3. A device for examining a body by gamma rays or X-rays comprising a radiation source, a diaphragm device arranged between said radiation source and said body, wherein said diaphragm device comprises a plurality of apertures for forming a plurality of primary beams, each of said primary beams having associated at least one slit and at least one detector device in said diaphragm device for intercepting scattered radiation from said primary beam passing through said diaphragm device, said at least one detector device being shielded to prevent striking of said at least one slit and at least one detector device by scattered radiation from other primary beams, wherein said diaphragm device includes a plurality of movable diaphragm parts, said movable diaphragm parts shifting said primary beams in parallel directions.

4. A device according to claim 3, wherein said movable diaphragm parts are rotatable.

5. A device according to claim 3, wherein said detector devices include at least two adjacent elongated detectors, said detectors and the associated said at least one slit extending parallel to directions of shift of said primary beams.

6. A device according to claim 3, claim 4 or claim 5, wherein said at least one detector device is disposed between said radiation source and said body to be examined.

7. A device according to claim 6, wherein a common housing encloses said diaphragm device and said at least one detector device, said common housing including said plurality of apertures for said primary beams, and a plurality of chambers provided with slits at a side of said common housing remote from said radiation source, said scattered radiation reaching said at least one detector device by said slits.

* * * * *